United States Patent
Hoell

(10) Patent No.: US 10,379,019 B2
(45) Date of Patent: Aug. 13, 2019

(54) METHOD AND DEVICE FOR HARDNESS TESTING

(71) Applicant: Qness GmbH, Golling an der Salzach (AT)

(72) Inventor: Robert Hoell, Scheffau (AT)

(73) Assignee: QNESS GMBH, Golling an der Salzach (AT)

( * ) Notice: Subject to any disclaimer, the term of this patent is extended or adjusted under 35 U.S.C. 154(b) by 43 days.

(21) Appl. No.: 15/674,806

(22) Filed: Aug. 11, 2017

(65) Prior Publication Data
US 2018/0045629 A1 Feb. 15, 2018

(30) Foreign Application Priority Data
Aug. 12, 2016 (AT) .............................. A 50734/2016

(51) Int. Cl.
*G06K 9/00* (2006.01)
*G01N 3/48* (2006.01)
(Continued)

(52) U.S. Cl.
CPC ............... *G01N 3/02* (2013.01); *G01B 11/02* (2013.01); *G01B 21/02* (2013.01); *G01B 21/16* (2013.01);
(Continued)

(58) Field of Classification Search
CPC ...................................................... G01N 3/40
See application file for complete search history.

(56) References Cited

U.S. PATENT DOCUMENTS

| | | | | |
|---|---|---|---|---|
| 6,301,956 B1* | 10/2001 | Fujita | ....................... | G01N 3/42 73/78 |
| 2004/0096093 A1* | 5/2004 | Hauck | ..................... | G01N 3/08 382/141 |

(Continued)

FOREIGN PATENT DOCUMENTS

| | | |
|---|---|---|
| CN | 2575657 Y | 9/2003 |
| CN | 201007701 Y | 1/2008 |

(Continued)

OTHER PUBLICATIONS

Jan. 8, 2018, EP communication issued for related EP application No. 17182031.
(Continued)

*Primary Examiner* — Rebecca A Volentine
(74) *Attorney, Agent, or Firm* — Young & Thompson

(57) ABSTRACT

In a method and device for setting one or more measuring points on a specimen in a specimen holder for automated hardness testing in a hardness-testing device, the hardness-testing device has a table, a tool holder with a penetrator and at least one lens. The specimen holder with the specimen is positioned on the table in the x- and y-directions. The table and/or tool holder can be moved in the z-direction, relative to one another. A virtual three-dimensional model of the specimen holder and specimen is selected from data storage, and the model and/or an overview image of the specimen is depicted on a screen. Then, a point is marked in the image, and one or more measuring point is/are automatically defined based on the measuring method selected. To each measuring point, the z-coordinate is automatically assigned in the hardness-testing device based on its x- and y-coordinates and virtual model.

20 Claims, 4 Drawing Sheets

Figure 1:
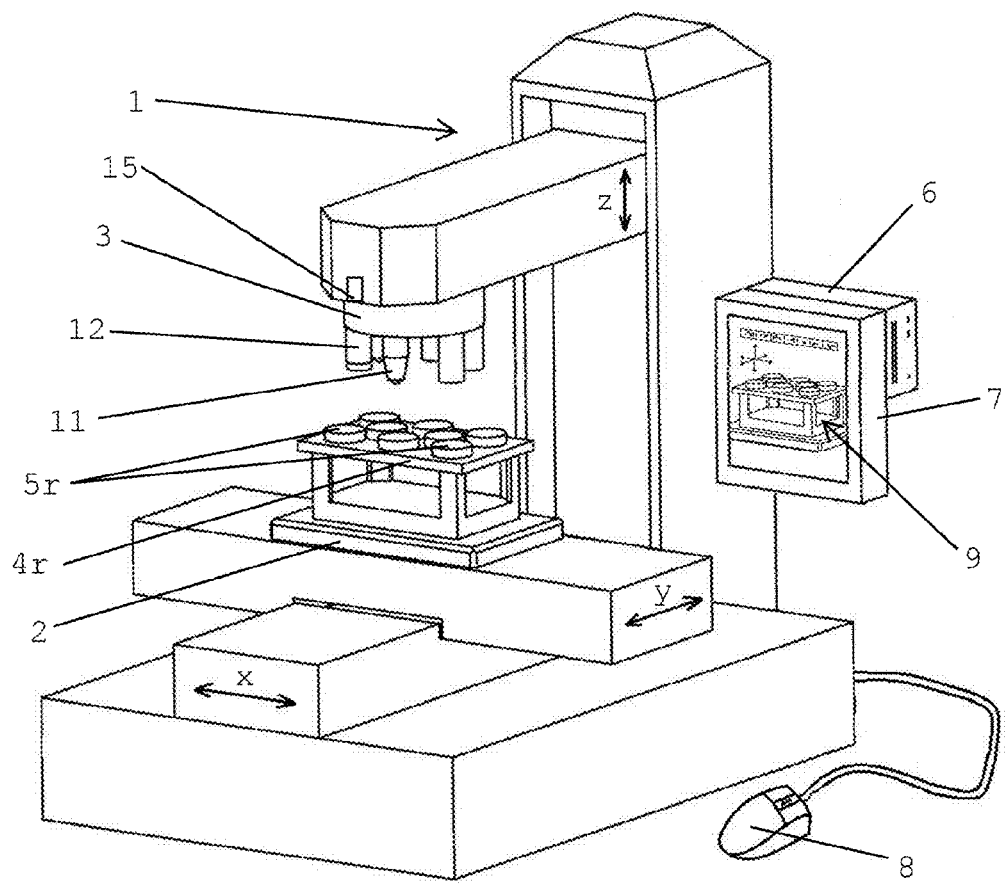

(51) Int. Cl.
*G01N 3/42* (2006.01)
*G01N 3/32* (2006.01)
*G01N 3/02* (2006.01)
*G01B 21/02* (2006.01)
*G01B 11/02* (2006.01)
*G01B 21/16* (2006.01)
*G06T 7/13* (2017.01)
*G06T 7/60* (2017.01)
*G06T 15/10* (2011.01)

(52) U.S. Cl.
CPC ....... *G01N 3/42* (2013.01); *G01N 2203/0286* (2013.01); *G01N 2203/0298* (2013.01); *G01N 2203/0647* (2013.01); *G06T 7/13* (2017.01); *G06T 7/60* (2013.01); *G06T 15/10* (2013.01); *G06T 2200/24* (2013.01)

(56) References Cited

U.S. PATENT DOCUMENTS

| | | | |
|---|---|---|---|
| 2007/0217672 A1* | 9/2007 | Shannon | G06T 7/0006 382/152 |
| 2012/0085154 A1 | 4/2012 | Takemura et al. | |
| 2012/0210777 A1* | 8/2012 | Holl | G01N 3/42 73/81 |
| 2014/0078299 A1* | 3/2014 | Kataoka | G01N 3/42 348/137 |
| 2014/0294282 A1* | 10/2014 | Miyakura | G06T 7/001 382/141 |
| 2016/0018308 A1* | 1/2016 | Kataoka | G01N 3/42 73/82 |
| 2016/0299498 A1* | 10/2016 | Valenzuela | H04N 5/23293 |

FOREIGN PATENT DOCUMENTS

| | | |
|---|---|---|
| CN | 204536142 U | 8/2015 |
| CN | 205067206 U | 3/2016 |
| DE | 42 19 848 A1 | 12/1992 |
| DE | 102011084102 A1 | 4/2012 |
| DE | 102014104704 A1 | 10/2014 |

OTHER PUBLICATIONS

AT Search Report, dated Jul. 11, 2017, from corresponding AT application No. A 50734/2016.

* cited by examiner

METHOD AND DEVICE FOR HARDNESS TESTING

The invention relates to a method for setting one or more measuring points on at least one specimen in a specimen holder for automated hardness testing in a hardness-testing device, whereby the hardness-testing device has a table, a tool holder with at least one penetrator and at least one lens, and optionally an overview image camera and a screen, whereby the specimen holder can be positioned on the table in the x- and y-directions and whereby the table and/or the tool holder of the hardness-testing device can be moved in the z-direction, relative to one another.

Moreover, the invention relates to a hardness-testing device.

For programming a hardness-testing device that is known from the state of the art, many individual steps must be set manually or many processes must be defined manually. For example, after the clamping of the specimen in a specimen holder and the positioning of this specimen holder in the x- and y-directions, i.e., in the horizontal plane, on or with the table of the hardness-testing device, the height of the specimen must be scanned or measured, whereby different sensors can be used on the tool holder. An operator must introduce, monitor and/or manually carry out this process of height determination in the z-direction. Then, the surface of the specimen must be focused using additional sensors on the tool holder or with one or more lenses, so that as sharp an image of the specimen as possible can be created. In this case, the operator must in turn actively intervene by setting the position at which the camera that is arranged on the tool holder is positioned for taking the image. Because of the inputs to be entered by the operator to the hardness-testing device or to a control connected to the hardness-testing device, a good deal of time is required, primarily since the operator in the case of the movement of the tool holder between two positions in most cases does not traverse the shortest and thus most time-saving path, i.a., also therefore since it must be ensured to avoid a collision between tool holder and/or tool and specimen. This is primarily the case for measurements of specimens that have a three-dimensional geometry that is pronounced in the z-direction.

The object of the invention is to provide a method of the above-mentioned type that simplifies the setting of one or more measuring points on at least one specimen. In particular, time is thus to be saved and, by minimizing the risk of a tool holder and specimen colliding, damage to the hardness-testing device and specimens can be prevented.

This object is achieved according to the invention with a method that has the features of claim 1, with a hardness-testing device that has the features of claim 15, and with a control that has the features of claim 16.

A special advantage of the invention lies in the fact that in an electronic data storage device associated with the hardness-testing device, one or more virtual three-dimensional models of one or more specimens or one or more specimen holders are stored and are provided for the method. Unlike what is known from the state of the art, in the hardness-testing device, a z-coordinate is also assigned to each set point that is established manually or with computer support, in particular to each measuring point, in addition to an x- and a y-coordinate based on the three-dimensional model that is provided. The tool holder of the hardness-testing device can be automatically positioned above and at an appropriate distance from the specimen with lens(es), penetrator(s) and optionally sensor(s) arranged thereon. The path that the tool holder must traverse for this purpose can be optimized, by which time is saved, and the risk of a tool holder colliding with a specimen or specimen holder is excluded.

The method according to the invention for setting one or more measuring points is performed, for example, as follows:

In a first step, a virtual three-dimensional model of a specimen holder is selected from an electronic data storage device, on which model at least one virtual three-dimensional model of a specimen that is selected from the electronic data storage device is arranged, so that a virtual three-dimensional model of a specimen holder with a specimen is provided. It is also conceivable that an already completely assembled model of a specimen holder with at least one specimen from the electronic data storage device is provided. Theoretically, only a specimen could also be selected, when no specimen holder is necessary, without exceeding the scope of the invention.

Previously or subsequently, the specimen holder, equipped with at least one specimen, is positioned on the table of the hardness-testing device. This position can be fixed in advance. In the same manner, however, it is conceivable that the position is read in by means of sensors or cameras and a suitable image-detection program, or that the position of the specimen holder and the specimen in the hardness-testing device is manually set.

For the case that no image, in particular no overview image and/or detail image, of the specimen is created in the entire method, since the measuring point(s) is/are set only on the three-dimensional model or its depiction on the screen, it plays no role when the specimen holder with the specimen is placed on the table. In this special case, the specimen holder with the specimen can also be placed first on the table, shortly before automated hardness testing is performed.

In a preferred embodiment of the method, an overview image can be taken after the placing or positioning of the specimen holder, equipped with the specimen, with an overview image camera arranged on the hardness-testing device, preferably in the area of the tool holder. It would also be conceivable that a lens arranged on the tool holder, which lens optionally automatically focuses on the specimen surface, takes a single overview image or several images, which are combined into a single overview image.

In a next method step, the model of the specimen holder with the specimen or the overview image is depicted or displayed on a screen. In terms of the invention, in this case, the display by other optical and electronic display means, such as, for example, projectors, is also considered to be visualization on a screen.

In an advantageous further development of the method, the depictions of the virtual three-dimensional model and the overview image can be superimposed. This additional possible function allows an optical testing, in which it can be found whether the correct model for the specimen holder and/or the specimen from the data storage device was provided, and/or whether the position of the specimen holder and/or specimen on the table is correct. Optionally, the position of the specimen on the table can then be corrected until it coincides with the position of the virtual model on the screen. As an alternative to this, it would also be conceivable to rotate or move the depiction of the virtual model manually until a match is achieved. In a further development of the method, a match can also be achieved automatically by means of a digital detection of the real specimen and an automatic, digital correction of the depiction of the virtual model by a control.

In the next method step according to the invention, a point on the depiction of the model and/or the overview image is marked on the screen using a suitable electronic input means, such as, for example, a keyboard, a computer mouse, or a touch screen. Subsequently in the method, this point is a reference point, starting point, intermediate point or end point for multiple measuring points (optionally a measurement series) or a reference point or measuring point for an individual measurement.

In an alternative embodiment of the method, it would be conceivable to set the position of the point in the x- or y-direction based on parameters that are to be input manually. In terms of the invention, in one embodiment, the control automatically marks a point with the input x- and y-coordinates.

Before the marking of a point, the specimen in the specimen holder can be rotated manually and/or automatically (by the specimen holder being correspondingly embodied) in order to be able to set one or more points or measuring points along a curved surface in the case of a specimen, embodied, for example, as a rotating body.

In a further step—before, during or after the point is marked—a measuring method is assigned to the method according to the invention.

In an especially preferred embodiment of the method, the measuring method is selected manually from a measuring method list that is preferably stored in the electronic data storage device. It would be conceivable to select standardized measuring methods, such as, for example, a single-point, serial, CHD, SHD or surface point measurement, or else even non-standardized measuring methods.

In an alternative embodiment, the assignment of the measuring methods can also be done automatically, for example by a measuring method being set in the preliminary stage or by only the execution of a single measuring method being possible, which in terms of the invention also is considered as automatic assignment of a measuring method.

In a preferred embodiment of the method, in another method step, an enlarged, real detail image of the section in which the point is arranged is taken and prepared or depicted using a camera by a lens located on the tool holder. For this purpose, the tool holder with the lens, optionally after a lens change, can be positioned automatically over the point, whereby a collision between a lens and a specimen holder with a specimen is prevented by the geometry of the specimen holder with a specimen known from the virtual model. The lens with known optical properties can automatically advance to the point or measuring point and/or focus the latter by the z-coordinate of the measuring point that is calculated from the virtual model, whereupon a camera assigned to the lens automatically takes a detail image. In this case, it is conceivable to depict the detail image on the screen overlaying the model and/or the overview image, preferably arranged in the area of the position of the point, optionally to superimpose the overview image with the detail image.

An embodiment of the method in which the detail image is used to manually correct the position of the point on the specimen surface is especially advantageous, whereby it is optionally possible to zoom in further into the detail image. For correction, the point in the detail image of the specimen can be moved, for example, in the x-direction and/or the y-direction. It is also conceivable to use different digital tools, such as automatic outer-edge detection, to correct the position of the point in the detail.

In order to set the point, in an alternative embodiment of the method, in particular when an overview image and/or detail image is not used, it is possible to zoom in only into the depiction of the model. Because of possible inaccuracies of the placement of the specimen holder, the position of the point, only using the virtual model, has in general but at most an accuracy of +/−0.2 mm.

In a next method step according to the invention, a measuring point or several measuring points is/are automatically defined. Based on the assigned measuring method and the location or position of the marked and optionally position-corrected point, (an) x- and y-coordinate(s) is/are assigned to the measuring point or measuring points, and in connection with the three-dimensional model, (a) known or deducible z-coordinate(s) is/are also assigned in the hardness-testing device.

Depending on the assigned measuring method, the point can be a reference point or starting point, away from which one or more measuring point(s) is/are defined at a set distance and in a set direction. A measurement series can thus be defined automatically. The point, however, can also be an individual measuring point by itself or one of multiple measuring points, which can be combined to form a measurement series. The required parameters for distance/distances and direction/directions are set either automatically or manually, for example in the case of the manual assignment of the measuring method.

In a further step of the method according to the invention, the x-, y- and z-coordinates of each defined measuring point are stored in the electronic data storage device. In this case, as storage devices in terms of the invention, both a temporary storage of the coordinates in, for example, a working storage device and a permanent storage in a long-term storage device, e.g., a hard disk or an SD [secure digital] memory card, are considered.

In a further development of the method according to the invention, specific method steps, such as, for example, the depiction, assignment of a measuring method, marking of a point, defining of measuring points and storage of the coordinates of measuring points, as well as method steps that take place in between, are repeated any number of times. The thus set measuring points can be stored in the electronic data storage device, and several measuring points can optionally be linked automatically or manually to a measurement series.

Before the setting of another point, the specimen in the specimen holder can be rotated manually and/or automatically (optionally repeatedly).

Subsequently, according to the invention, an impression can be automatically created at each set measuring point by means of a penetrator arranged on the tool holder, meaning that a number of impressions are produced that correspond to the number of measuring points.

In the case of multiple measuring points, the penetrator can be positioned automatically and in an optimized order on the shortest path of the series according to the measuring points and can create impressions. In this optimized order of movement, the risk of a tool or tool holder colliding with the specimen or the specimen holder can be automatically excluded, since the geometry of the specimen holder with the specimen on one side and the tool holder with the tools on the other side is known.

In terms of the invention, it is conceivable that the impressions are created at the measuring points with different penetrators, whereby the penetrators can create different forms of impressions. As penetrators, all possible penetrators, known in particular for standardized measuring methods, such as, for example, a Vickers pyramid, a Knoop pyramid, a Brinell ball or other penetrators, can be used, depending on requirements or the measuring method to be performed.

The gauging of the impressions can be performed in the case of the invention subsequently directly in connection with the creation of the impressions or else at a later time. This takes place preferably fully automatically by the computer-supported control, but can also be performed on a screen with manual support, whereby the approach to the measuring points can also be further optimized in a computer-supported manner.

A hardness-testing device according to the invention—which is especially suitable for executing the method according to the invention, with a table, a tool holder with at least one penetrator and at least one lens, optionally with an overview image camera and a screen, whereby a specimen holder can be positioned on the table in the x- and y-directions and the table and/or the tool holder can be moved relative to one another in the z-direction—has, according to the invention, an electronic data storage device with at least one virtual three-dimensional model and at least one measuring method, as well as a control that determines the z-coordinates of the measuring point from specified x- and y-coordinates of a measuring point based on the model.

One or more penetrators, lenses, cameras and/or sensors can be arranged on the tool holder of the hardness-testing device. The tool holder can be designed, for example, as a turret, in order to make possible a quick change between the individual tools (one or more penetrators and one or more lenses) arranged thereon. Other tool holders, for example in the form of swivel elements, can also be used.

An overview image camera can be arranged on the tool holder itself, in the area of the tool holder or else also at any other matching site of the hardness-testing device.

The control can carry out all automatic and automated method steps, in particular computer-supported or computer-implemented steps. It consists of, for example, a computer unit with control software adapted to the method steps. Sensors arranged on the tool holder or on other sites of the hardness-testing device can be connected to the control and can convey information to the control.

Preferred and advantageous embodiments of the invention are subjects of the other subclaims.

Figure 2:
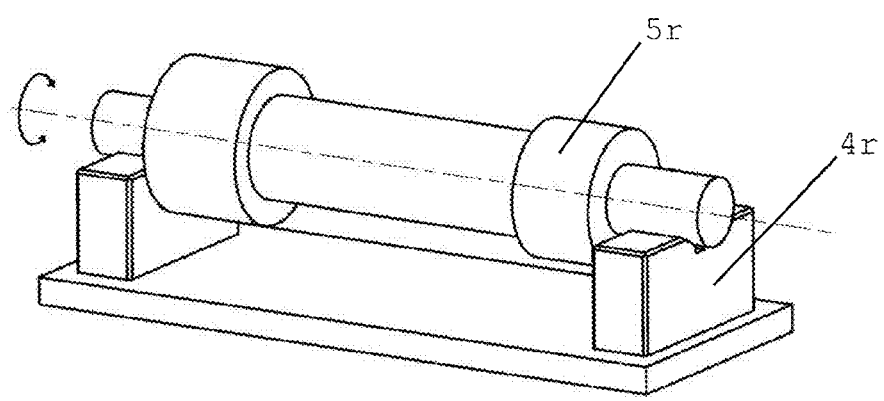
Figure 3:
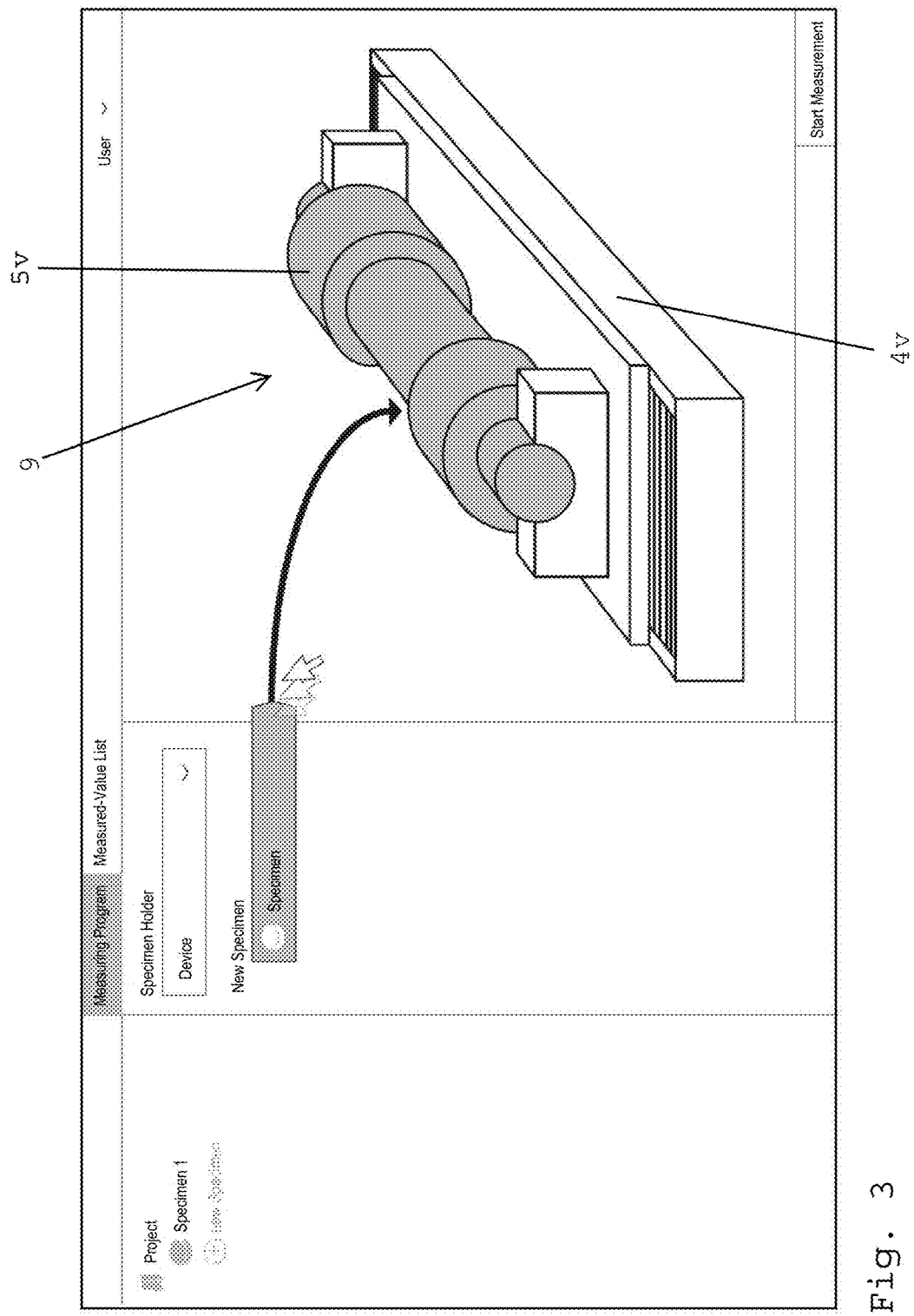
Figure 4:
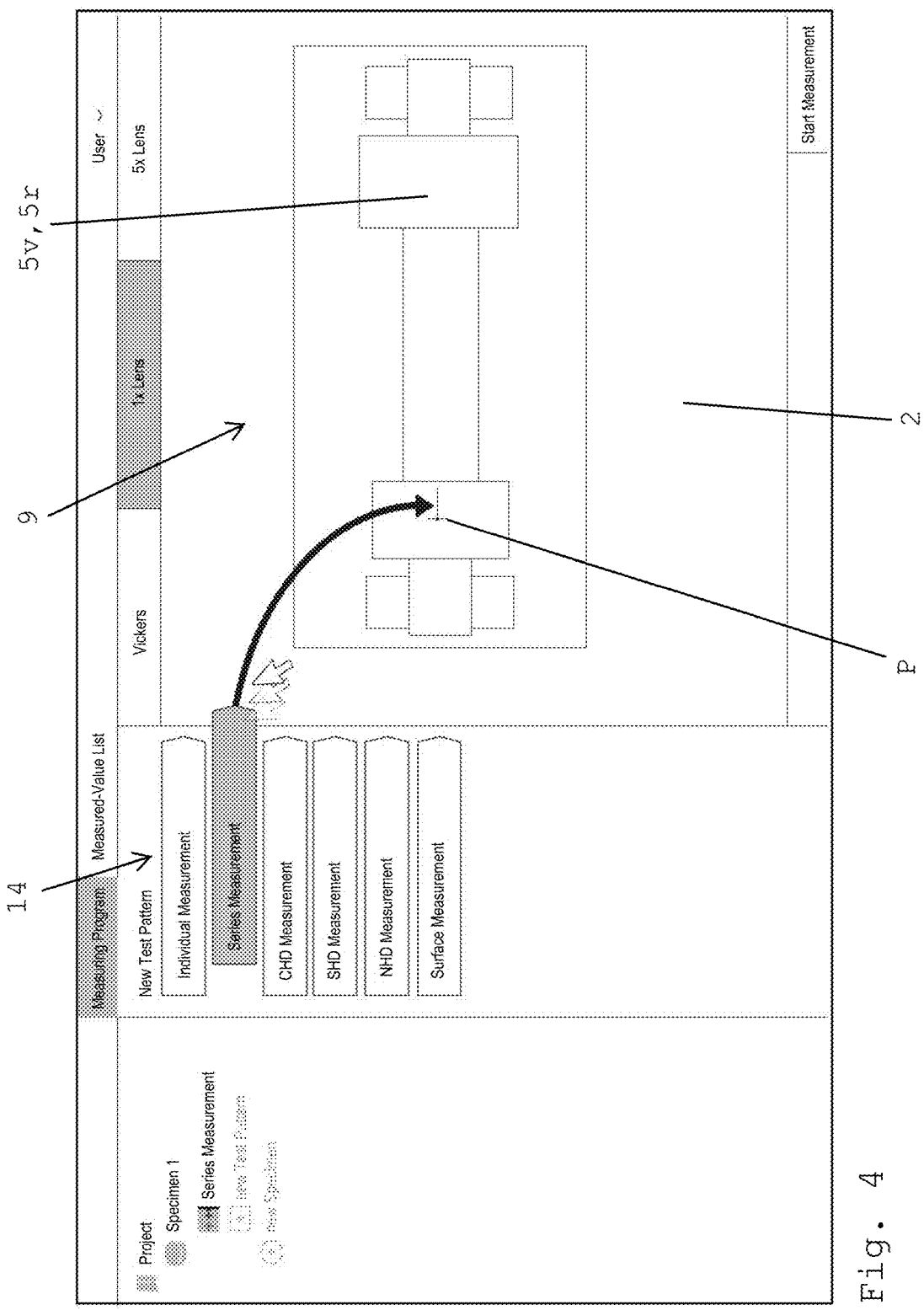
Figure 5:
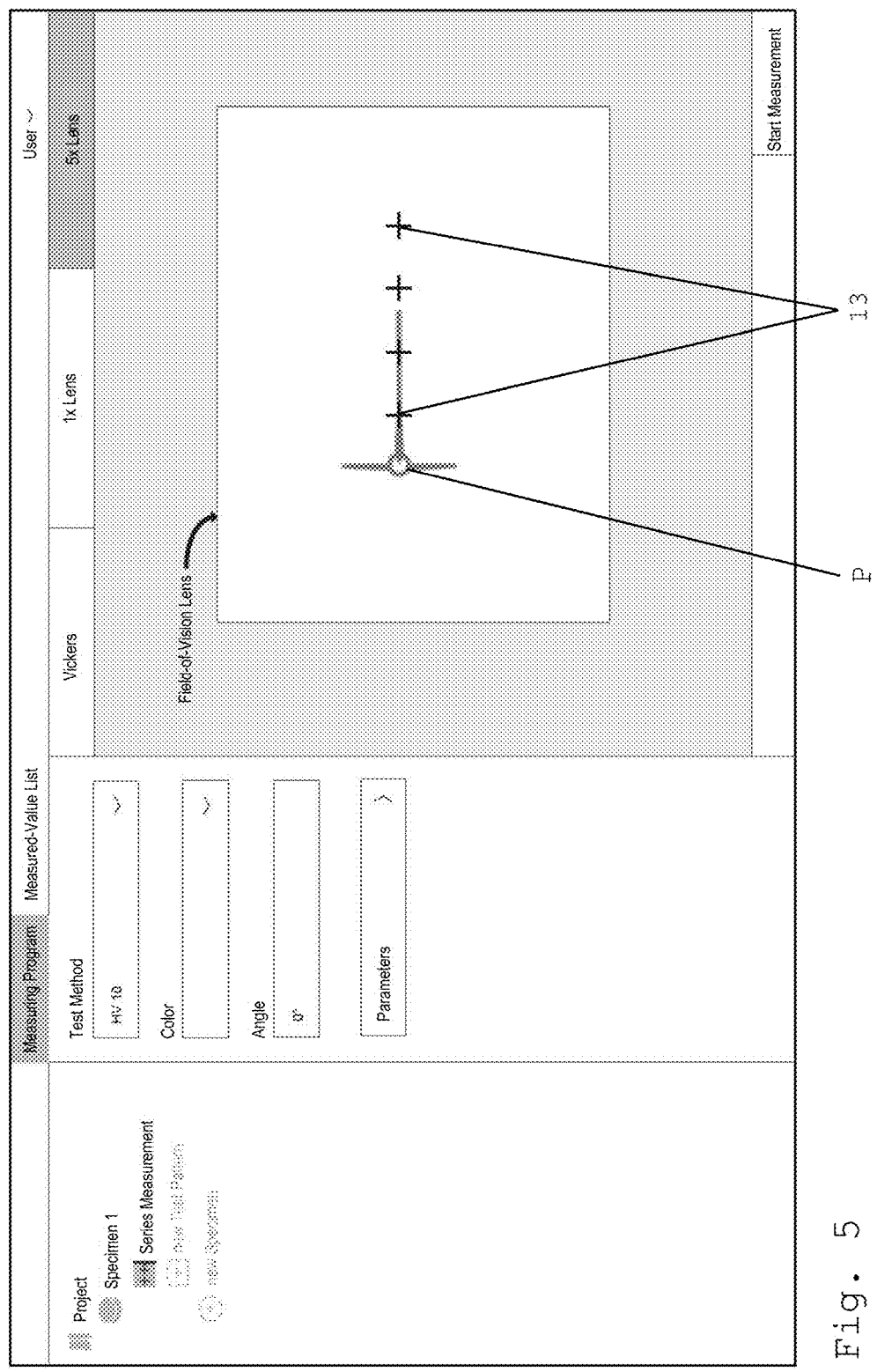

Other details, features, and advantages of the invention follow from the description below with reference to the attached drawings, in which preferred embodiments of the invention are depicted. Here:

FIG. 1 shows an isometric view of a hardness-testing device according to the invention, on which a specimen holder with several specimens is placed, FIG. 2 shows another embodiment of a specimen holder with a single, rotationally-symmetrical specimen, FIG. 3 shows a step of the method according to the invention, in which a virtual three-dimensional model is provided, FIG. 4 shows another step of the method according to the invention, in which a point is marked on the model, and FIG. 5 shows still another step of the method according to the invention, in which the position of the point is depicted on an enlarged image and can be corrected.

FIG. 1 shows a hardness-testing device 1, according to the invention, with a table 2 that can be positioned in the x- and y-directions and a tool holder 3 that can be moved in the z-direction. A possible embodiment of a specimen holder 4r with specimens 5r is positioned on the table 2.

The hardness-testing device 1 has a control 6 with an electronic data storage device for virtual three-dimensional models 9 and a screen 7, e.g., a touch screen. For easier operation, an electronic input means 8, such as, for example, a keyboard and/or a computer mouse, can also be connected to the control 6.

Multiple tools, such as one or more penetrators 11, one or more lenses 12 and optionally sensors, are arranged on the tool holder 3. In addition, in the area of the tool holder 3, an overview image camera 15 is arranged.

FIG. 2 shows by way of example another embodiment of a specimen holder 4r with a rotationally-symmetrical specimen 5r.

In FIG. 3, a method step is depicted, in which an already previously selected and prepared virtual specimen holder 4v is equipped with a virtual specimen 5v that is optionally selected from a list, and thus a virtual three-dimensional model 9 is provided from the electronic data storage device and is depicted on the screen 7.

FIG. 4 shows the depiction of the virtual three-dimensional specimen 5v on the screen 7, which is depicted superimposed by an overview image of the real specimen 5r taken by an overview camera 15. This makes possible a monitoring of the selection of the virtual model 9 or the virtual specimen 5v and the position of the real specimen 5r on the table 2, which exactly match in the depicted embodiment.

In FIG. 4, it is depicted how a measuring method (e.g., series measurement) is subsequently selected from a list 14 using the electronic input means 8 and the computer program running in the control 6 of the hardness-testing device 1, and a point P is marked in the depiction of the specimen 5v, 5r. If necessary, of course, a penetrator can also still be selected before or after.

Then, after the tool holder 3 with a lens 12 was automatically positioned over the point P of the real specimen 5r, a detail image—automatically taken by the lens 12 and enlarged—of the section of the real specimen 5r can be depicted with the point P on the screen 7, as FIG. 5 shows. The position of the point P can then be corrected using computer-implemented tools and/or the electronic input means 8 in the x- and y-directions. The computer-implemented tool can be, for example, an outer-edge-detection program, with which an edge is automatically detected and a distance to this edge is set.

Depending on the selected measuring method, a measuring point 13 is defined at the position of the point P and/or one or more measuring points 13 is/are defined at positions at some distance therefrom on the surface of the specimen 5r. To each measuring point 13, the control 6 assigns x- and y-coordinates, and, based on the known three-dimensional geometry of the model, also the z-coordinates in the hardness-testing device 1, whereby the coordinates of each measuring point 13 are stored in the electronic data storage device.

Then, the actual hardness testing can be performed in a single measurement or a measurement series, as known per se from the state of the art, whereby according to the invention—in particular in the case of measurement series—however, a course that is guaranteed collision-free and is optimized with respect to the path of the tool holder 3 is ensured.

It should be pointed out that the individual method steps do not absolutely have to be carried out in the order indicated in the claims, if not for functional reasons, the execution of a method step absolutely requires the previous execution of another method step.

In summary, an embodiment of the invention can be described as follows:

Method and device for setting one or more measuring points 13 on a specimen 5r in a specimen holder 4r for automated hardness testing in a hardness-testing device 1, whereby the hardness-testing device 1 has a table 2, a tool holder 3 with at least one penetrator 11 and at least one lens 12. The specimen holder 4r with the specimen 5r can be positioned on the table 2 in the x- and y-directions, and the table 2 and/or the tool holder 3 of the hardness-testing device 1 can be moved in the z-direction, relative to one another. A virtual three-dimensional model 9 of the specimen holder 4v with a specimen 5v arranged thereon is selected from an electronic data storage device, and the model 9 and/or an overview image of the specimen 5v, 5r is depicted on a screen 7. Then, a point P is marked in the depiction on the screen 7, and one or more measuring point(s) 13 is/are automatically defined based on the selected measuring method, whereby to each measuring point 13, based on its x- and y-coordinates and the virtual model 9, the z-coordinate is automatically assigned in the hardness-testing device 1.

The invention claimed is:

1. A method for setting one or more measuring points (13) on at least one specimen (5r) in a specimen holder (4r) for automated hardness testing in a hardness-testing device (1), whereby the hardness-testing device (1) has a table (2), a tool holder (3) with at least one penetrator (11) and at least one lens (12), and optionally an overview image camera (15) and a screen (7), whereby the specimen holder (4r) can be positioned on the table (2) in the x- and y-directions, and whereby the table (2) and/or the tool holder (3) of the hardness-testing device (1) can be moved in the z-direction, relative to one another, the method comprising:
   a) selection and provision of a virtual three-dimensional model (9) of the specimen holder (4v) with at least one specimen (5v), arranged thereon, from an electronic data storage device,
   b) positioning of the specimen holder (4r), equipped with the specimen (5r), on the table (2),
   c) automatic depiction of the model (9) and/or an overview image, prepared from the specimen (5r), on the screen (7),
   d) assignment of a measuring method,
   e) marking of a point (P) in the depiction of the model (9) and/or the overview image of the specimen (5r) on the screen (7),
   f) automatic defining of one or more measuring point(s) (13) based on the measuring method, whereby in the hardness-testing device (1) to each measuring point (13), x- and y-coordinates are automatically assigned based on the position of the point (P) and the assigned measuring method, and z-coordinates are assigned based on the virtual model (9), and
   g) automatic storage of the x-, y- and z-coordinates of each measuring point (13) in a data storage device.

2. The method according to claim 1, wherein the measuring method in step d) is automatically assigned.

3. The method according to claim 1, wherein the measuring method in step d) is manually assigned, selected in particular from a measuring method list (14) stored in a data storage device.

4. The method according to claim 1, wherein step c) is preceded by a step c0), in which automatically an overview image of the specimen (5r) is created by the overview image camera (15) or by assembling several individual images taken by the lens (12).

5. The method according to claim 4, wherein before step c0), the specimen (5r) is positioned below the overview image camera (15) or the lens (12) on the tool holder (3).

6. The method according to claim 4, wherein after step c), a step c1) follows, in which the virtual model (9) is automatically superimposed on the screen (7) with the overview image of the specimen (5r).

7. The method according to claim 1, wherein after step e), a step e1) follows, in which an enlarged detail image of a section of the specimen (5r) is depicted with the point (P) on the screen (7).

8. The method according to claim 7, wherein before step e1), the lens (12) is positioned automatically over the point (P).

9. The method according to claim 7, wherein after step e1), a step e2) follows, in which the position of the point (P) on the enlarged detail image of the section of the specimen (5r) is corrected manually and/or with computer support and/or automatically, for example with an outer-edge-detection program, in the x-direction and/or y-direction.

10. The method according to claim 1, wherein the specimen (5r) is automatically and/or manually rotated before step e).

11. The method according to claim 1, wherein the steps c) to g) and optionally the rotation of the specimen (5r) are repeated.

12. The method according to claim 11, wherein stored measuring points (13) are linked manually and/or automatically to a measurement series.

13. The method according to claim 1, wherein for performing the hardness testing, a number of impressions corresponding to the number of measuring points (13) is created automatically by means of the penetrator (11).

14. The method according to claim 13, wherein at least one impression created by the penetrator (11) is measured with automatic and/or manual support.

15. A hardness-testing device (1), for executing the method according to claim 1, with the hardness-testing device comprising a table (2), a tool holder (3) with at least one penetrator (11) and at least one lens (12), optionally with an overview image camera (15) and a screen (7), whereby a specimen holder (4r) is positionable on the table (2) in both the x- and y-directions, and the table (2) and/or the tool holder (3) can be moved relative to one another in the z-direction, wherein the hardness-testing device (1) has an electronic data storage device with at least one virtual three-dimensional model (9) and at least one measuring method, as well as a control (6), which determines the z-coordinate of the measuring point (13) from specified x- and y-coordinates of a measuring point (13) based on the model (9).

16. A computerized control unit (6) operatively connected to a hardness-testing device (1) comprising a table (2), a tool holder (3) with at least one penetrator (11) and at least one lens (12), optionally with an overview image camera (15) and a screen (7), whereby a specimen holder (4r) is positionable on the table (2) in both the x- and y-directions, and the table (2) and/or the tool holder (3) can be moved relative to one another in the z-direction, wherein the hardness-testing device (1) has an electronic data storage device with at least one virtual three-dimensional model (9) and at least one measuring method, wherein the computerized control unit (6) determines the z-coordinate of the measuring point (13) from specified x- and y-coordinates of a measuring point (13) based on the model (9) for executing the automated method steps according to claim 1.

17. The method according to claim 5, wherein the positioning of the specimen is performed automatically based on the model (9).

18. The method of claim 17, wherein the specimen (5*r*) is automatically focused based on the model (9).

19. The method according to claim 7, wherein the enlarged detail image is focused based on the z-coordinates.

20. The method according to claim 8, wherein the lens (12) is positioned automatically over the point (P) after an automatic lens change.

\* \* \* \* \*